(12) United States Patent
McCabe

(10) Patent No.: US 6,372,045 B1
(45) Date of Patent: Apr. 16, 2002

(54) APPARATUS FOR PREPARING SAMPLE CARTRIDGES FOR A PARTICLE ACCELERATION DEVICE

(75) Inventor: Dennis McCabe, Middleton, WI (US)

(73) Assignee: Powderject Vaccines, Inc, Madison, WI (US)

(*) Notice: Subject to any disclaimer, the term of this patent is extended or adjusted under 35 U.S.C. 154(b) by 0 days.

(21) Appl. No.: 09/313,578

(22) Filed: May 12, 1999

Related U.S. Application Data

(63) Continuation of application No. PCT/US97/20817, filed on Nov. 13, 1997, and a continuation-in-part of application No. 08/747,870, filed on Nov. 13, 1996, now Pat. No. 5,733,600.

(51) Int. Cl.[7] .............................................. B05C 19/04
(52) U.S. Cl. ...................... 118/308; 118/318; 118/320
(58) Field of Search ................................ 118/306, 308, 118/318, 320, 55

(56) References Cited

U.S. PATENT DOCUMENTS

| | | | |
|---|---|---|---|
| 4,151,064 A | * 4/1979 | Kuehnle | 118/320 |
| 4,298,634 A | 11/1981 | Phelps | |
| 4,597,995 A | 7/1986 | Snow et al. | |
| 4,822,692 A | 4/1989 | Koehler | |
| 4,945,050 A | 7/1990 | Sanford | |
| 4,987,013 A | 1/1991 | Atkins et al. | |
| 5,015,580 A | 5/1991 | Christou et al. | |
| 5,120,657 A | 6/1992 | McCabe et al. | |
| 5,149,655 A | 9/1992 | McCabe et al. | |
| 5,204,253 A | 4/1993 | Sanford et al. | |
| 5,372,761 A | 12/1994 | Anderson, Sr. | |
| 5,405,779 A | 4/1995 | McCabe et al. | |
| 5,584,807 A | 12/1996 | McCabe et al. | |
| 5,665,444 A | * 9/1997 | Eguchi et al. | 118/318 |
| 5,738,725 A | * 4/1998 | Bernstein, Jr. | 118/318 |
| 5,780,100 A | 7/1998 | McCabe et al. | |

FOREIGN PATENT DOCUMENTS

| | | |
|---|---|---|
| EP | 0 301 749 A2 | 5/1988 |
| EP | 0 362 863 A2 | 4/1990 |
| WO | WO 96/12513 | 5/1996 |

OTHER PUBLICATIONS

Klein, T.M., et al., "Particle Gun Technology: A Novel Method for Introduction of DNA into Living Cells," *Biotechnology in Plant Science: Relevance to Agriculture in the Eighties*, Abstract for Post 28 (1985).

Klein, T.M., et al., "High Velocity Microprojectiles for Delivering Nucleic Acids into Living Cells," *Nature* 327:70–73 (1987).

Klein, T.M., et al., "Stable Genetic Transformation of Intact Nicotiana Cells by the Particle Bombardment Process," *Proc. Natl. Acad. Sci. USA* 85:8502–8505 (1988).

McCabe, D.E., et al., "Stable Transformation of Soybean (Glycine max) by Particle Acceleration," *Bio/Technology* 6:923–926 (1988).

Sanford, J.C., "The Biolistic Process," *TIBTECH* 6:299–302 (1988).

Sanford, J.C. et al., "Delivery of Substances into Cells and tissues Using a Particle Bombardment Process," *Particulate Science and Techn.* 5:27–37 (1987).

\* cited by examiner

*Primary Examiner*—Laura Edwards
(74) *Attorney, Agent, or Firm*—Thomas P. McCracken

(57) ABSTRACT

Particles coated with a therapeutic agent are deposited onto the inner surface of a length of tubing using a process which includes introducing the particles into the tubing while the tubing is rotating horizontally. An apparatus for performing the process is also disclosed.

17 Claims, 2 Drawing Sheets

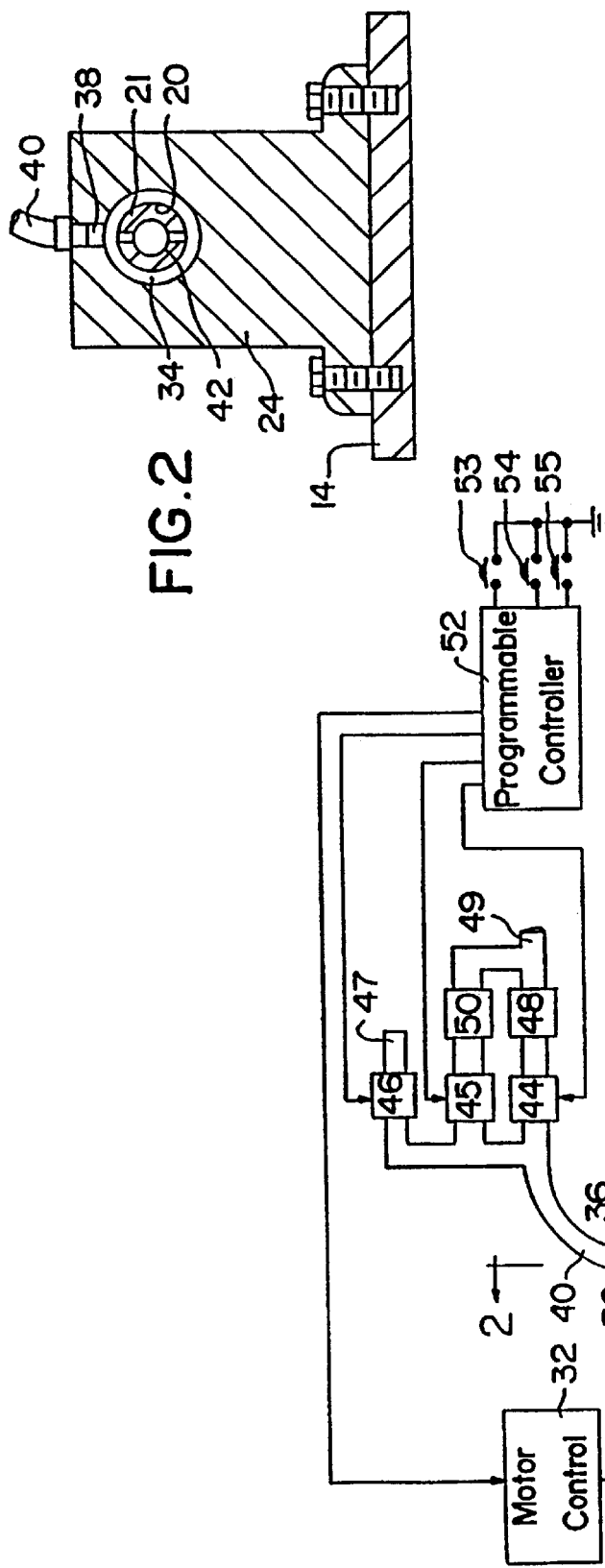
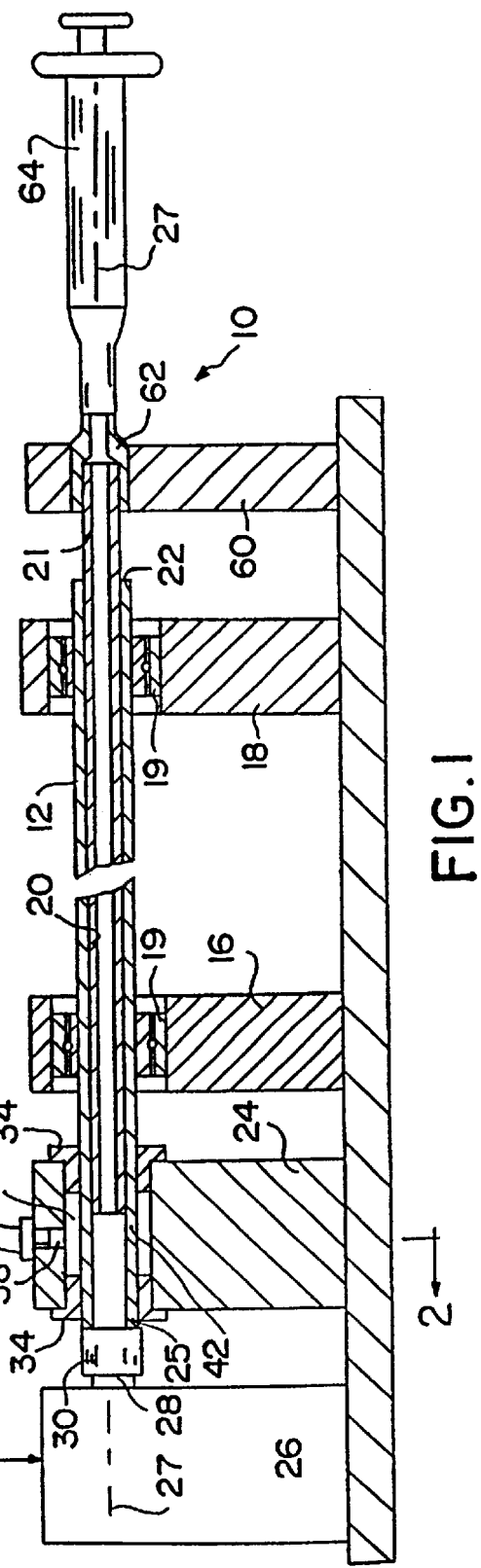
FIG.2
FIG.1

```
                    START
                      │
                      ▼
         ┌──────────────────────────┐
         │ COAT PARTICLES WITH      │
         │ BIOLOGICAL MATERIAL      │
         └──────────────────────────┘
                      │
                      ▼
         ┌──────────────────────────┐
         │ ROTATE TUBING AT 50-200 RPM │
         └──────────────────────────┘
                      │
                      ▼
         ┌──────────────────────────┐
         │ OPEN VENT VALVE          │
         └──────────────────────────┘
                      │
                      ▼
         ┌──────────────────────────┐
         │ INTRODUCE PARTICLE       │
         │ SOLUTION INTO TUBING     │
         └──────────────────────────┘
                      │
                      ▼
         ┌──────────────────────────┐
         │ CLOSE VENT VALVE         │
         └──────────────────────────┘
                      │
                      ▼
         ┌──────────────────────────────────┐
         │ ROTATE AT 2000 RPM FOR 15 SECONDS │
         └──────────────────────────────────┘
                      │
                      ▼
         ┌──────────────────────────────────────────┐
         │ ROTATE AT 1000 RPM FOR 55 SECONDS        │
         │ AND OPEN GAS VALVE FOR 2.5-3.5 ml/min    │
         └──────────────────────────────────────────┘
                      │
                      ▼
         ┌──────────────────────────────────────────┐
         │ ROTATE AT 5000 RPM FOR 2 MINUTES         │
         │ AND OPEN GAS VALVE FOR 500-800 ml/min    │
         └──────────────────────────────────────────┘
                      │
                      ▼
                     END
```

FIG. 3

APPARATUS FOR PREPARING SAMPLE CARTRIDGES FOR A PARTICLE ACCELERATION DEVICE

CROSS REFERENCE TO RELATED APPLICATIONS

This application is a continuation of International Application No. PCT/US97/20817, filed Nov. 13, 1997, designating the United States, from which priority is claimed pursuant to 35 U.S.C. §365(c) and a continuation-in-part of application Ser. No. 08/747,870, filed Nov. 13, 1996, now U.S. Pat. No. 5,733,600, from which application priority is claimed pursuant to 35 U.S.C. §120, and which applications are incorporated herein by reference in their entireties.

TECHNICAL FIELD

The present invention relates to the field of particle delivery. More particularly, the invention relates to a particle-mediated delivery method and apparatus for delivering materials into a target cell.

BACKGROUND OF THE INVENTION

In the past decade, particle-mediated acceleration of biological and pharmaceutical materials, particularly genetic material, into living cells and tissue, has emerged as an important tool for use in the fields of plant and animal biotechnology. Transient expression and germ line integration of introduced DNA has been demonstrated in microorganisms, plants, and animals.

As the fundamentals of the technology have been elucidated, attention has increasingly shifted toward development of devices that enable one to perform particle-mediated delivery of biological materials sequentially, and in rapid succession. Such a device would be particularly advantageous for use in mass immunization of humans or domesticated animals with various vaccine compositions.

To that end, an instrument has been developed for accelerating particles coated with biological substances using compressed gas as the motive force. The biological materials are deposited upon the surface of small, dense particles of a carrier material, such as gold or platinum, which may be spherically shaped. The coated carrier particles are then coated onto the interior curved surface of a rigid tube or cartridge. The coated tube or cartridge is loaded into the instrument and aligned with a barrel. Upon release from a suitable source, compressed gas is passed through the coated tube and the barrel, which picks up the carrier particles and accelerates the same toward a target surface.

Thus it is advantageous to uniformly coat the interior of the tube with particles that carry the biological sample and to produce the same uniform coating on numerous tubes.

SUMMARY OF THE INVENTION

It is a general object of the present invention to provide a method and an apparatus for forming a large number of particle cartridges for use in a gas driven particle acceleration instrument. A further object of the invention is to provide such a method and an apparatus which uniformly coats the cartridges with the particles.

In one embodiment, an apparatus is provided for depositing particles within a length of tubing. The apparatus comprises a tubing roller having an elongate tubing bore formed therein, wherein said bore has first and second ends and is sized for removable insertion of a length of tubing therein. A means for rotating the tubing roller about the major axis of the tubing bore is also provided, and a gas delivery means, which comprises a chamber with an inlet for introducing gas from an associated source into the chamber, and an aperture through which a portion of the tubing roller extends. The aperture provides fluid communication between the second end of the tubing bore and the chamber. A support means is arranged adjacent to the first end of the tubing bore, wherein the support means provides for the sealable engagement between an end of a length of tubing inserted into the tubing bore and an associated source of particles to be deposited within the length of tubing.

In another embodiment, a method-is provided for depositing particles in a length of tubing having a longitudinal axis and a curved interior surface. The method comprising the following steps:

(a) preparing a uniformly dispersed suspension of particles coated with a biological substance in an evaporable liquid;
(b) rotating the tubing about its longitudinal axis at a first speed;
(c) introducing the particle suspension into the tubing while rotating said tubing at the first speed;
(d) rotating the tubing to centrifugally separate the particles from the evaporable liquid and distribute the particles on the interior surface of the tubing; and
(e) passing a gas through the tubing as the tubing rotates to dry the particles distributed on the interior surface.

It is an advantage of the present invention that a large number of substantially identical sample cartridges can be prepared in a single effort. The present centrifugal method produces tubes that are very uniform, as compared to previous techniques, and lends itself to automation of the process.

These and other objects, features and advantages of the present invention will become apparent from the following specification, read in light of the accompanying drawings.

BRIEF DESCRIPTION OF THE DRAWINGS

FIG. 1 is a cut-away view of an apparatus constructed according to the present invention.

FIG. 2 is a cross-sectional view taken along line 2—2 in FIG. 1.

FIG. 3 is a flowchart depicting the sequence of steps in a process for depositing coated particles within a: tubular sample cartridge.

DETAILED DESCRIPTION OF THE PREFERRED EMBODIMENT

Before describing the present invention in detail, it is to be understood that this invention is not limited to a particular particle delivery device, or to particular carrier particles as such may, of course, vary. It is also understood that different embodiments of the disclosed sample method and apparatus may be tailored to the specific needs in the art. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms “a”, “an”, and “the” include plural referents unless the content clearly dictates otherwise. Thus, for example, reference to “a particle” includes reference to mixtures of two or more particles, reference to "a therapeutic agent" encompasses one or more such agents, reference to "a bearing mount" includes one or more such mounts, and the like.

A. Definitions

Unless defined otherwise, all technical and scientific terms used herein have the same meaning as commonly understood by one of ordinary skill in the art to which the invention pertains. The following terms are intended to be defined as indicated below.

As used herein, the term "therapeutic agent" intends any compound or composition of matter which, when administered to an organism (human or nonhuman animal) induces a desired pharmacologic, immunogenic, and/or physiologic effect by local, regional, and/or systemic action. The term therefore encompasses those compounds or chemicals traditionally regarded as drugs, vaccines, and biopharmaceuticals including molecules such as proteins, peptides, hormones, nucleic acids, gene constructs and the like. Such therapeutic agents may be used prophylactically to prevent disorders and/or for the treatment of on-going disorders.

More particularly, the term "therapeutic agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; centralnervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

Particles of a therapeutic agent, alone or in combination with other drugs or agents, are typically prepared as pharmaceutical compositions which can contain one or more added materials such as vehicles, and/or excipients. "Vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone,.gelatin, waxes, and like materials.

Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

B. The Deposition Apparatus

The present invention provides a reproducible method for mass producing sample cartridges for use in a gas-driven particle acceleration instrument. In particular, small dense carrier particles are reversibly coated onto a concave inner surface of a sample cartridge. The carrier particles are themselves reversibly coated with a therapeutic agent, for example, a biological substance such as genetic material or a protein. During particle acceleration and delivery, a gas stream passing over the carrier particles releases the same from the inner surface of the sample cartridge, and carries the particles to a target cell, tissue, or organism.

For repeatability of delivery, it is important that the number of particles delivered from each sample cartridge be ascertainable and relatively constant, at least within a statistically acceptable range, for example, within about ±10% of an experimentally determined mean number. It is also important that particle distribution among the sample cartridges be kept substantially constant, thus maximizing sample-to-sample reproducibility.

Referring now to FIG. 1, a suitable apparatus 10 is shown which can be used in the deposition procedure described herein. The apparatus 10 comprises a tubing roller 12 which is rotatably mounted to a base 14 in a generally horizontal orientation by two or more mounts, depicted at 16 and 18. The base 14 can be of any size and shape, and should be at least as long as the length of tubing to be coated in the practice of the present invention.

The base 14 can include leveling means and a spirit level to facilitate the horizontal positioning of the tubing roller. The mounts 16 and 18 are attached to, or part of, the base 14, and comprise bearing mounts, indicated at 19, which engage and retain the tubing roller 12 in its horizontal position in the apparatus. The bearing mounts 19 can be of any suitable type, e.g., roller, ball or needle type, so long as they allow precise rotation of the tubing roller 12 about its major axis with minimal friction. The mounts 16 and 18 are preferably rotatably engaged with the tubing roller 12 at opposing ends thereof. Depending upon the length of the tubing roller 12, additional mounts may be provided between the terminally positioned mounts 16 and 18 as needed to prevent excessive vibration in the tubing roller at the relatively high rotational speed used during the coating process.

The tubing roller 12 can be formed of any substantially rigid, durable material such as metal, plastic, wood or the like. In the embodiment depicted in FIG. 1, the tubing roller 12 is cylindrical. In addition, the tubing roller 12 has sufficient length along the axis of rotation to receive and secure substantially the entire length of a piece of tubing which is to be coated.

The mounted tubing roller 12 has an axis of rotation which is coaxial with the major axis thereof, and an elongate tubing bore 20 which is coaxial with the axis of rotation. The tubing bore 20 is positioned so that a length of tubing 21 received therein shares the same axis of rotation as the tubing roller 12 and extends into the tubing roller through an opening 22 at a first end of the tubing bore. The tubing bore 20 is sized in length, width, and depth, to accommodate a variety of tubing types, and preferably is generally cylindrical. To facilitate insertion of the tubing 21 into the tubing bore 20, the opening 22 of the tubing bore can be wider than the bore 20 itself and preferably flares outward from the bore 20. A second opening 25 in the tubing bore 20 is capped. The tubing bore 20 extends along the rotational axis 27 of the apparatus 10.

The capped second end of the tubing bore passes through a gas delivery mount 24 and engages a means 26 for rotating the tubing roller 12 about the axis of rotation (i.e., about the major axis of the elongate tubing bore). The rotator means 26 can be powered in any way, for example, using electrical or mechanical energy to effect the direct or indirect rotation of the tubing roller 12. However, the rotator must provide sufficient power to rotate the tubing roller 12 about the axis of rotation at various constant rates between about 50 and 6000 revolutions per minute (RPM) for at least about two minutes. The rotator means 26 can be connected to any portion of the tubing roller 12, so long as the axial rotation of the roller is not unduly constrained. In one configuration, a shaft 28 of the rotator means 26 is directly attached via a fitting 30 to the capped second end 25 of the tubing bore. A suitable rotator means 26 that can attach directly to the shaft 28 is an electrically actuated gear motor, such as a Barnant Mixer Series 20 motor, which can be remotely controlled using an associated variable speed motor control, indicated at 32. The rotator means 26 need not be attached to the base 14, but can be attached thereto to provide for increased stability during operation of the apparatus.

S As described above, a portion of the tubing roller 12 passes through a gas delivery mount 24 as shown in FIGS. 1 and 2. The gas delivery mount provides a gas delivery means for introducing gas into the tubing bore 20. More particularly, the tubing roller 12 extends through an aperture in the gas delivery mount 24 and is sealably supported within the aperture by a pair of bushings 34 which are formed of a durable, low friction material. The bushings 34 seal off the opening of the aperture, and thus help define a chamber 36 within the gas delivery mount. Alternatively, sealed bearings may be utilized in place of bushings 34, as long as the sealed bearings can operate at the rotational speeds used in the method of the present invention. An inlet passage 38 is provided in the gas delivery mount 24. The inlet passage 38 allows for introduction of a flow of gas from an associated source into the chamber 36, for example via gas conduit 40. A transverse aperture 42 extends through the tubing roller 12 to provide fluid communication between the chamber 36 and the tubing bore 20, thereby allowing gas from the chamber to enter the tubing bore. The chamber 36 extends completely around the tubing roller 12 so that communication between the gas conduit 40 and the chamber 36 can remain constant while the tubing roller is spun about axis 27 by the rotator means 26. Thus, the gas delivery mount 24 enables continuous, uninterrupted delivery of a drying gas from an associated external source of gas into the second end of the bore 20 at a suitably controlled flow rate.

The gas conduit 40 can be connected to one or more gas valves in order to provide for controlled delivery of gas into the apparatus 10. In the apparatus of FIG. 1, three electrically operated solenoid valves 44, 45 and 46, are connected to the gas conduit 40 to provide for variable rates of gas delivery into the apparatus. The inlet side of the first valve 44 is coupled to a first flow regulator 48 which allows gas to flow therethrough at a first, fixed rate, for example between about 2.5–3.5 ml/minute. Similarly the inlet side of the second valve 45 is coupled to a second flow regulator 50 which allows gas to flow therethrough at a second fixed rate, for example between about 500–800 ml/minute. The two flow regulators are connected via a supply hose 49 to a source of a compressed drying gas, such as air or nitrogen. As can be seen, the first valve/regulator combination provides a first gas delivery path into the chamber 36, and the second valve/regulator combination provides a second gas delivery path into the chamber. The third valve 46 is used as an outlet for the chamber 36, and connects the gas conduit 40 to an atmospheric exhaust port 47.

Operation of the components of the deposition apparatus 10 may be controlled manually, but preferably is governed by a commercially available programmable controller 52. The programmable controller 52 has outputs connected to the speed control device 32 and the three solenoid valves 44–46. Inputs of the programmable controller 52 can be connected to three push button switches 53, 54 and 55, by which buttons a technician designates operating modes of load, spin and stop, respectively. As will be appreciated by the skilled artisan upon reading the instant specification, a microprocessor unit can be used to direct operation of the programmable controller, allowing for fully automated operation of the deposition apparatus 10. For example, an appropriate set of spin cycle times, rotational rates, and drying gas flow rates, can be entered into the microprocessor, which then controls operation of the controller 52 over an entire deposition procedure. Alternatively, the microprocessor allows for semiautomatic operation of the deposition apparatus 10, such as where one or several cycles of the deposition procedure are under the control of the microprocessor, while parameters of other operations are controlled manually.

C. Particle Preparation

The process by which carrier particles (coated with a therapeutic agent) are deposited on the inner surface of a length of tubing is depicted in the flowchart of FIG. 3. The first step in the process involves coating the carrier particles with the therapeutic agent.

Therapeutic agents (or pharmaceutical preparations derived therefrom) can be coated onto carrier particles using a variety of techniques known in the art. Dense materials are preferred in order to provide particles that can be readily accelerated toward a target over a short distance, wherein the coated particles are still sufficiently small in size relative to the cells into which they are to be delivered. It has been found that carrier particles having an average diameter of a few microns can readily enter living cells without unduly injuring such cells.

Methods for coating the small, dense particles with a biological substance are also known. Any such method can be used to prepare the coated particles, however a preferred method for coating DNA onto gold particles is described herein. One of ordinary skill in the art will appreciate from the following description the importance of determining, within acceptable tolerance limits, the amount of biological substance per particle and the number of particles per sample cartridge. The acceptable tolerance levels should be about ±30%, preferably about ±20%, and even more preferably about ±10% of the desired amount.

Gold particles are preferred for coating with DNA. References herein to “beads” or “particles” are intended to include, without limitation, both spherical and amorphous particles of appropriate size and density. DNA is a preferred biological substance for coating onto particles. However, other substances including, but not limited to, RNA and proteinaceous materials can also be coated onto particles using the following techniques. In this regard, conditions for depositing other biological substances or for using non-gold particles can vary from the method stated in ways that are understood in the art.

Continuing with the particle preparation method, a desired amount of gold particles is placed in a centrifuge tube. The amount of gold used can be roughly determined by multiplying the desired number of particles per delivery by the number of sample cartridges being prepared, e.g., the number of cartridges produced from one piece of tubing 21. A suitable amount of particles per delivery is typically on the order of about 0.25 to 0.50 mg of gold particles per delivery, although acceptable amounts can be higher or lower. By routine experimentation, one can ascertain limits on particle delivery amounts below which the transfer is acceptably high (by any ascertainable measure, such as gene expression level or biological response to treatment) while the trauma target tissues is minimal. Minimal trauma in an animal target tissue is evidenced by only a slight reddening of the target area.

One representative method for preparing DNA-coated particles is as follows. A small volume (100 to 300 ml) of 0.1 M spermidine is added to the centrifuge tube and a suspension of nonagreggated particles is formed by sonicating the tube contents for a sufficient length of time, generally for a few seconds.

Next, an appropriate volume of DNA, suspended in a buffer that does not affect its integrity or stability, is added to the particle/spermidine suspension to achieve an acceptable DNA loading rate. The DNA, spermidine, and gold particles are mixed by vortexing. The DNA loading rate is the average density of DNA per particle, expressed for a bulk population (e.g., $\mu$g DNA per mg of particles). Preferred effective DNA loading rates on gold particles range from about 0.1 to 5.0 $\mu$g DNA per mg gold particles. Exceeding 10.0 $\mu$g DNA per mg gold is not preferred as it can lead to clumping of the gold particles. However, as little as 0.001 $\mu$g DNA per mg of gold is adequate to achieve significant expression from some expression vectors.

In order to obtain the most uniform coating results, the volume of DNA should not exceed the volume of spermidine, but smaller volumes may be used. Accordingly, it may be necessary to adjust either the concentration of DNA or the volume of spermidine added initially to the gold particles.

Calcium chloride ($CaCl_2$) is then added to the mixture during gentle vortexing. A sufficient-amount of the $CaCl_2$ is added to result in precipitation of DNA-coated gold particles. If 2.5 M $CaCl_2$ is added, a suitable volume is equal to the volume of spermidine added earlier. The mixture is allowed to precipitate at room temperature for at least five or ten minutes. At DNA loading rates of 1.0 $\mu$g DNA per mg gold particles, or higher, precipitation should be apparent immediately after the $CaCl_2$ is added.

After precipitation, the tube is centrifuged briefly (10–15 seconds) to pellet the coated gold particles. The supernatant is removed and discarded and the pellet is washed several times with a suitable solvent (e.g., ethanol) until virtually all of the water has been removed from the coated particle preparation. Between each solvent wash, the preparation is spun and the supernatant discarded. The coated particles of the final pellet, containing known amounts of both DNA and gold, are resuspended in an evaporable liquid, preferably 100% ethanol, optionally containing an appropriate amount of an additive that provides a slight, temporary adhesive effect sufficient for joining the coated particles to the sample cartridge. One such suitable adhesive is polyvinyl pyrrolidone (PVP). The amount of adhesive required in the evaporable liquid depends upon the gas pressure which the sample cartridges will be exposed to during subsequent particle acceleration, and also upon the type of tubing used. For delivery operations at gas pressures ranging from about 100 to 150 psi, no adhesive is required. For operation at about 150 to 300 psi, PVP at 0.001 to 0.01 mg per ml of the particle preparation is appropriate. PVP at 0.01 to 0.05 mg per ml is suitable for operations at pressures ranging from about 300 to 500 psi or higher. At operation pressures of about 500 to 800 psi, 0.3 mg per ml PVP will provide a suitable adhesive effect.

Some care should be taken in determining the total volume in which to resuspend the coated particles. The volume depends upon the desired amount of biological substance per delivery, the actual DNA loading rate, the desired particle density in the final sample cartridge, and the internal volume per length of tubing. One of ordinary skill will also recognize that the preferred amount of DNA per delivery, and the amount of particles per delivery, will vary with the nature of the target, the density at which the particles are coated, and the desired outcome of the transfer (e.g. transient expression or stable integration). Therefore, each of the stated variables, including the concentration at which the particles are loaded into the tubing, should be adjusted accordingly.

After settling upon a desired particle is loading rate, particle density, and volume capacity per unit length of tubing, one can readily determine the total volume of the evaporable liquid in which to resuspend the coated particles. A suitable sample cartridge length has been found to be about a 12.7 mm length of tubing having an internal capacity of between about 0.6 and 2.0 ml per 17.78 cm length. For tubing with this particular internal capacity, a simple calculation demonstrates that if 0.5 mg of gold is desired in a 12.7 mm sample cartridge, the particles are prepared at a concentration of 7.0 mg gold per ml. Likewise, for a 0.25 mg sample in a 12.7 mm cartridge, a 3.5 mg per ml concentration is appropriate. Concentrations that achieve other particle densities are calculated in the same way.

To achieve complete transfer of the coated particles into the evaporable liquid, it is recommended that the pellet be transferred to the storage tube in several partial transfer steps. For example, the coated particles can be resuspended in a small volume (500 ml) of the liquid, vortexed, briefly sonicated (2–3 seconds), and then transferred to a clean tube. It is recommended that the tube be formed of a material to which the biological substances do not stick, such as a polypropylene culture tube. These small volume transfers can be repeated until all of the coated particles have been transferred to the tube. If desired, the tubes containing suspended coated particles can be sealed with Parafilm and stored for several months at −20° C. When the coated particles have been completely transferred, preparation of the sample cartridges can begin. Previously stored tubes should be warmed to room temperature before unsealing for use in the following tube coating method.

Cartridge Loading Process

To prepare sample cartridges, a length of suitable tubing having a concave arcuate inner surface is filled with a uniform suspension of the coated particles dispersed within the evaporable liquid. It is preferred that the tubing is transparent or translucent so that particles coated onto the inner concave surface can be visually observed. All tubing used should be inert to reaction with the selected drying gas (preferably nitrogen) and should be sufficiently durable to retain mechanical stability throughout the particle delivery process. Tefzel® tubing (1/8" outer diameter x 3/32" inner diameter) has been found to be a suitable tubing substrate for use in the practice of the invention. A 17.78 cm length of this particular size of tubing has an internal capacity of about 0.8 ml.

Referring to again to FIG. 1, when the deposition apparatus is turned off, a length of tubing 21 can be inserted through opening 22 into the tubing bore 20 such that the tubing closely engages the surface of the bore and the two components will rotate together. A portion of the tubing 21 is left projecting from the opening 22 of the bore 20. The amount of tubing that extends from the opening is selected such that the tubing will not be inserted too far into the tubing roller 12 where it could block gas flow into the chamber 36. A removable support 60 is then secured to the base 14 adjacent to the exposed end of the tubing 21. The support 60 comprises a slip bearing 62 which receives the exposed end of the tubing. The slip bearing 62 engages the outer surface of the tubing 21 in a manner that provides a fluid-tight seal between the end of the tubing and the support 60, while allowing the tubing to rotate within the slip bearing which remains stationary within the support.

A suspension of coated particles, prepared by a method such as that described above, is vortexed and sonicated to achieve a uniform distribution. A charge of the coated particle suspension is then drawn into a suitable delivery means, such as the barrel syringe 64 depicted in FIG. 1. As will be appreciated upon reading the instant specification, any suitable source of particles can be used, however, the barrel syringe provides for convenient measured delivery of a volume of the particle suspension. The syringe 64 has an resilient coupling that is adapted to fit onto an exposed end of the slip bearing 62 as shown in FIG. 1. In this manner, the support 60 provides for the sealable engagement between the exposed end of the tubing 21 and the syringe 64 for delivery of the particles which are to be deposited within the length of tubing.

With the filled syringe 64 attached to the slip bearing 62, the technician presses the "load" switch 53. Actuation of this switch causes the programmable controller 52 to open a vent valve 50, directs the speed control means 32 to activate the rotator means 26 which starts to turn the tubing roller 12 and the tubing 21 at a first speed, for example, 50 to 200 rpm. The plunger of the syringe 64 then is pushed by the technician to force the coated particles from the syringe into the tubing 21. By rotating the tubing upon delivery of the particle suspension from the syringe, the particles are prevented from setting to the bottom of the horizontally arranged tubing 21. In addition, venting the opposite end of the tubing via vent valve 50 prevents pressure build-up in the tube during introduction of the coated particles.

After the coated particles have been transferred to the tubing 21, the syringe 64 is removed from the slip bearing 62. Next, the technician presses the "spin" switch 54, which causes the programmable controller 52 to direct closure of the vent valve 50 and the speed control 32 to increase the rotational speed of the tubing roller to a second speed, for example about 1700 to 2300 rpm, with 2000 rpm being preferred. The tubing spins at this second rate for at least about 15 seconds which centrifugally forces the particles out of suspension and against the concave arcuate inner surface of the tubing 21, forming a uniform layer thereon.

After the layer forms, the settled particles are dried by first expelling the supernatant from the tubing. This is readily achieved by introducing a drying gas, such as air or nitrogen gas, into one end of the tubing. At this point, the programmable controller 52 automatically decreases the rotation speed of the tubing to between about 700 to 1300 rpm, with 1000 rpm preferred. At the same time, the first gas valve 44 is opened by the controller 52, which causes compressed gas from supply hose 49 to flow into the tubing roller 12 via the chamber 36 at a rate of about 2.5 to 3.5 ml per minute as determined by the setting of the first gas flow regulator 48. This gas flow blows the separated supernatant from the tubing 21 back through the slip bearing 62. Operation under these conditions continues for about 55 seconds which is sufficient to expel the supernatant, after which point the first gas valve 44 is closed.

Finally, the settled particles are dried by removing the residual evaporable liquid from the tubing 21. To accomplish this, the programmable controller 52 increases the speed of rotation to between about 4000 and 6000 rpm, with 5000 rpm being preferred. This causes increased centrifugal forces sufficient to separate the particles from the evaporable liquid. The second valve 45 is thus actuated by the controller 52, causing gas to flow into the tubing roller 12 at about 500 to 800 ml per minute as determined by the setting of the second gas flow regulator 48. This increased gas flow evaporates the liquid from the suspension, leaving a uniform dispersion of the coated particles adhered to the concave arcuate inner surface of the tubing 21. The final drying step lasts for approximately two minutes or until the particles are completely dry. After the drying cycle is finished, the programmable controller 52 closes the second gas valve 45 and directs the speed control 32 to stop the rotator means 26. The coated tubing 21 then may be removed from the deposition apparatus 10.

Before the tubing is cut into suitable lengths for use as sample cartridges, it is necessary to remove any end portions of the tubing in which particle distribution is uneven. The distribution of particles in the tubing can be tested operationally in using a gas driven particle acceleration apparatus under actual delivery conditions. The following test conditions are suitable, although other tests for determining and comparing the particle delivery profile of prepared sample cartridges can readily be devised.

Test cartridges of desired length are removed from opposite ends of the tubing. The particles from each test cartridge are delivered from the concave inner surface of the tubing under a gas pressure of around 400 psi, and are directed into minimal water (3%) agar in a 60 ml petri dish without surface condensation. From each plate, a slice approximately one cm long is cut through the center of the target agar and mounted onto a microscope slide. It is important to test slices of comparable thicknesses when samples are compared.

The slices are analyzed for particle delivery depth and particle number a microscope. The particles can be readily observed using a microscope having a 10× eyepiece equipped with a micrometer. At the top surface of the agar, the particles are most dense, with density decreasing along with the increasing depth of the agar slice. Areas of high, medium, and low particle density are noted in each slice. The eyepiece micrometer is aligned to zero at a depth approximately equal to the deepest penetration of the particles. The micrometer value at the agar surface is the particle depth. Typical particle depths after delivery into minimal water agar at 400 psi are about 100 to 120 $\mu$m when 0.95 $\mu$amorphous gold particles are used, and about 260 300 $\mu$m when 1 to 3$\mu$gold spherical particles or beads are used.

If particle depth and density are similar, cartridges derived from the tubing section between the ends are acceptable for use. However, should the two ends differ markedly from each other, or standard coating parameters, additional pairs of opposite end samples should be tested until both ends yield comparable acceptable results. When comparable results are obtained from both ends, the remaining length of tubing is cut into pieces of suitable length using a scalpel and a ruler or other type of cutting device. The sample cartridges can then be stored at 4° C. with desiccant in a Parafilm-sealed and labelled vial for up to two months.

Accordingly, a novel method and apparatus for depositing particles within a length of tubing have been described. Although preferred embodiments of the subject invention have been described in some detail, it is understood that obvious variations can be made without departing from the spirit and the die scope of the invention as defined by the appended claims.

We claim:

1. An apparatus for depositing particles within a length of tubing, the apparatus comprising:

a tubing roller having an elongate tubing bore formed therein, wherein said bore has first and second ends and is sized for removable insertion of a length of tubing therein;

means for rotating the tubing roller about the major axis of the tubing bore;

gas delivery means comprising a chamber with an inlet for introducing gas from an associated source into the chamber, said chamber further having an aperture through which a portion of tubing roller extends, wherein said aperture provides fluid communication between the second end of the tubing bore and the chamber; and support means arranged adjacent to the first end of the tubing bore, wherein said support means provides for a fluid-tight seal between an end of a length of tubing inserted into the tubing bore and an exposed end of the support means which sealably engages with an associated infection means or syringe containing the particles to be deposited within the length of tubing.

2. The apparatus of claim 1 further comprising a bearing mount for supporting the tubing roller while allowing the rotational motion thereof.

3. The apparatus of claim 1, wherein the means for rotating the tubing roller comprises a variable speed rotator.

4. The apparatus of claim 3, wherein the variable speed rotator comprises a motor driven by a variable speed control device.

5. The apparatus of claim 1 further comprising a first valve connected to the chamber inlet, wherein said first valve controls the passage of gas from the associated source into the chamber via a first gas delivery path.

6. The apparatus of claim 5 further comprising a second valve connected to the chamber inlet, wherein said second valve controls the passage of gas from the associated source into the chamber via a second gas delivery path.

7. The apparatus of claim 5 further comprising a first gas flow regulator which controls the flow of gas through the first valve.

8. The apparatus of claim 6 further comprising a first gas flow regulator which controls the flow of gas through the first valve, and a second gas flow regulator which controls the flow of gas through the second valve.

9. The apparatus of claim 8, wherein said first gas flow regulator limits gas flow through the first valve at a first rate, and said second gas flow regulator limits gas flow through the second valve at a second rate.

10. The apparatus of claim 1 further comprising a chamber outlet which provides a path through which gas can exit from the chamber.

11. The apparatus of claim 10 further comprising a third valve connected to the chamber outlet, wherein the third valve controls the passage of gas from the chamber to an exhaust means.

12. The apparatus of claim 6 further comprising a chamber outlet which provides a path through which gas can exit from the chamber.

13. The apparatus of claim 12 further comprising a third valve connected to the chamber outlet, wherein the third valve controls the passage of gas from the chamber to an exhaust means.

14. The apparatus of claim 13 wherein the means for rotating the tubing roller comprises a variable speed rotator, said variable speed rotator formed by the operative combination of a motor driven by a variable speed control device.

15. The apparatus of claim 14, wherein the first, second and third valves are solenoid valves.

16. The apparatus of claim 15, wherein the variable speed control device and the first, second and third valves are operably connected with a programmable controller which controls actuation of said valves and said variable speed control device, thereby providing for the automated operation of said apparatus.

17. The apparatus of claim 16 further comprising a microprocessor for controlling the operation of the programmable controller.

* * * * *